United States Patent [19]

Harmjanz

[11] Patent Number: 5,231,994
[45] Date of Patent: Aug. 3, 1993

[54] HOSE OR TUBULAR GUIDE CATHETER

[76] Inventor: Dietrich Harmjanz, Fuchswinkel 20, DE-3101 Gross Hehlen, Fed. Rep. of Germany

[21] Appl. No.: 870,188
[22] PCT Filed: Aug. 27, 1988
[86] PCT No.: PCT/EP88/00769
  § 371 Date: Jun. 23, 1989
  § 102(e) Date: Jun. 23, 1989
[87] PCT Pub. No.: WO89/03701
  PCT Pub. Date: May 5, 1989

Related U.S. Application Data

[63] Continuation of Ser. No. 635,804, Jan. 2, 1991, which is a continuation of Ser. No. 378,525, Jun. 23, 1989.

[30] Foreign Application Priority Data

Oct. 27, 1987 [DE] Fed. Rep. of Germany ....... 3736226

[51] Int. Cl.⁵ .................................... A61M 25/00
[52] U.S. Cl. .................. 128/772; 604/280; 128/658
[58] Field of Search ............ 128/651, 658, 772, 7, 128/341; 604/48, 53, 93, 264, 280, 281, 160, 166

[56] References Cited

U.S. PATENT DOCUMENTS

| | | | |
|---|---|---|---|
| 3,508,554 | 4/1970 | Sheridan | 604/280 |
| 4,490,138 | 12/1984 | Lipsky et al. | 604/264 |
| 4,531,943 | 7/1985 | Van Tassel et al. | 128/658 |
| 4,801,297 | 1/1989 | Mueller | 604/264 |
| 4,863,441 | 9/1989 | Lindsay et al. | 604/264 |

FOREIGN PATENT DOCUMENTS 3339179  5/1985  Fed. Rep. of Germany ...... 128/658

OTHER PUBLICATIONS

USCI a Division of C. R. Bard Inc., Pamphlet on Extracorporeal Circ. Cannulae & Vinyl Specialty Cath. p. 3.

Primary Examiner—Peter A. Aschenbrenner
Attorney, Agent, or Firm—Peter C. Richardson; Lawrence C. Akers; John L. LaPierre

[57] ABSTRACT

A hose or tubular guide catheter which accommodates and guides a balloon catheter through a portion of the vascular system to a site where the balloon catheter can be employed for the dilatation of coronary arteries. The wall of the catheter, in the region of its anterior end, is set back from the edge over a portion of the circumference. If the end of this guide catheter has passed only a little way into the entrance of a coronary artery, blood from the aorta can enter through the large flow section into the catheter and into the coronary artery. Hence the blood supply of the coronary artery is assured. By further advance of the guide catheter, the recess is closed off by the wall of the entrance opening of the coronary artery, so that injected contrast medium will enter full into the coronary artery and cannot pass into the aorta.

3 Claims, 2 Drawing Sheets

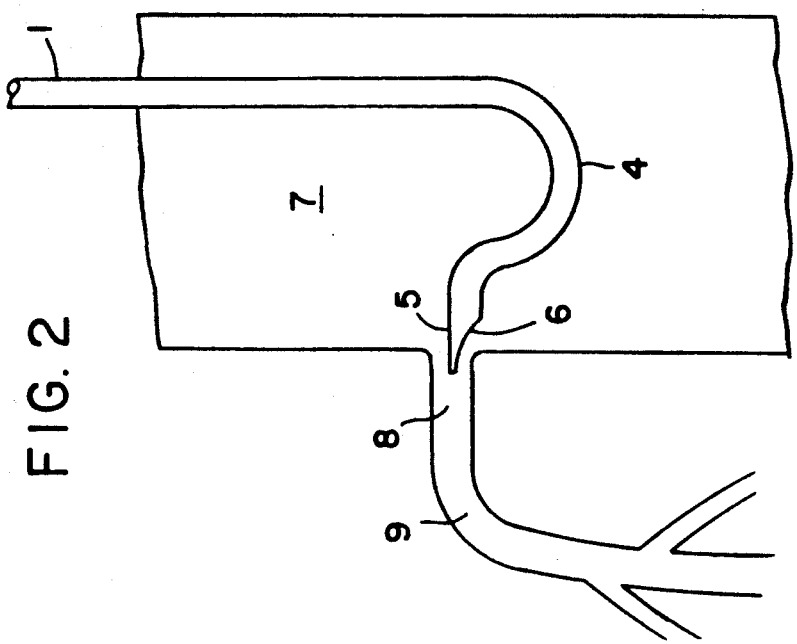
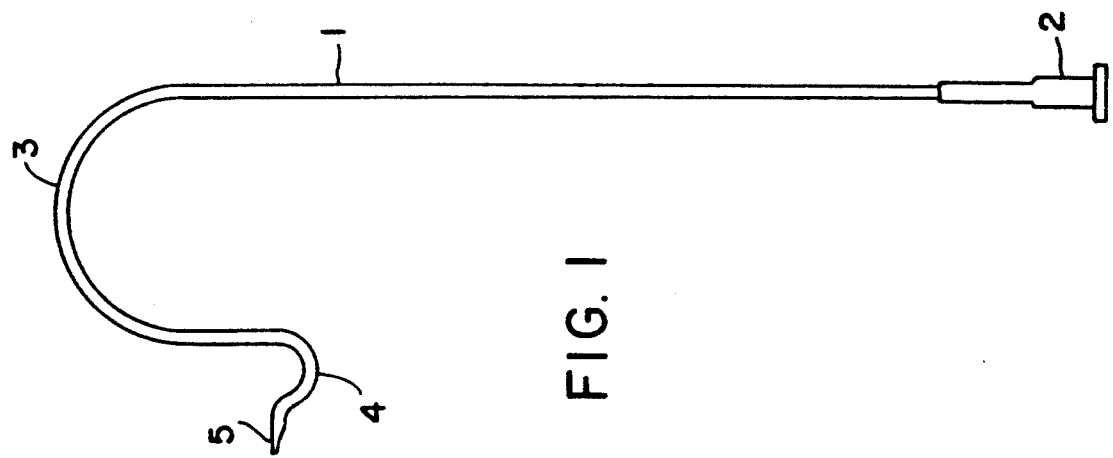

HOSE OR TUBULAR GUIDE CATHETER

This is a continuation of application Ser. No. 635,804, filed on Jan. 2, 1991 which is a continuation of Ser. No. 378,525 filed on Jun. 23, 1989.

BACKGROUND OF THE INVENTION

The invention relates to a hose or tubular guide catheter to accommodate and guide a balloon catheter for dilatation of coronary arteries of the heart.

From a printed source due to the firm of Schneider Medintag, Zurich, "Guide catheter with atraumatic tip," "Soft Touch" type, a hose or guide catheter of the kind in question is known whose end has an annular edge extending substantially axial to the axis of the catheter. In the immediate region of its end, the catheter has a more or less curved form, to facilitate insertion of the end from the aorta into the opening of a coronary artery, or at least render it possible. The guide catheter is moved manually so that its tip will enter a coronary artery and remain there, whereafter a guide wire is passed through the guide catheter into the coronary artery, and then a balloon catheter is introduced over the guide wire and through the guide catheter until the balloon arrives in the region of a constriction of the coronary artery, where the balloon, limited in diameter, is inflated and the constricted place in the coronary artery is thereby dilated and enlarged.

The diameter of the guide catheter is relatively large so that, with adequate wall thickness, a balloon catheter will pass through. This comparatively large diameter of the guide catheter leads in many cases to its tightly closing the entrance opening of the coronary artery, so that the blood supply of the coronary artery is blocked. The myocardium is thereby rendered ischemic with a risk of mortification.

To avoid this disadvantage, the said company print also mentions a guide catheter having lateral holes at some distance from its tip, through which blood is to enter the guide catheter from the aorta and pass on into the coronary artery. If these lateral openings are too close to the anterior edge of the guide catheter, there is danger that the openings will be located in the region of the coronary artery and thus be closed off by its walls, so that they cannot serve their purpose. If the lateral holes are more distant from the anterior edge of the tip of the guide catheter, blood can indeed flow in, but then there is the disadvantage that contrast medium to be injected into the coronary artery through the guide catheter for X-ray visualization of the artery will leak out of the lateral holes, be lost for purposes of visualizing the coronary artery, and impede or at least impair the X-ray image by entering the aorta. Besides, there is the disadvantage that the lateral holes tend to be clogged by blood clots.

SUMMARY OF THE INVENTION

The object of the invention is to provide a guide catheter of the kind in question, not subject to the disadvantages portrayed, that is, avoiding interruption of the blood supply to the coronary artery and the loss of contrast medium from the guide catheter into the aorta and at the same time not losing the desired guiding function.

That object of the invention is accomplished by the teaching specified in the characterizing clause of Claim 1.

The fundamental idea of that teaching is to provide the wall of the guide catheter in the anterior region with a slit, which may for example be prepared by simply cutting the catheter away laterally. If such a guide catheter is inserted in the entrance opening of a coronary artery just so far that the posterior end of the recess or slit is still located within the region of the aorta, than blood can flow from the aorta into the catheter and through it into the coronary artery. In this insertion position, the guide catheter can already perform its guiding function fully. If contrast media are to be introduced, the guide catheter may be advanced again briefly so that the recess or slit lies in the region of the entrance opening of the coronary artery throughout its full length, and is therefore largely closed off by the artery wall. This advance may take place briefly when contrast medium is injected. Then the guide catheter may be withdrawn again somewhat, so that blood can again enter as previously described through the recess of the wall of the guide catheter into the coronary artery.

The recess according to the invention may be of equal width in lengthwise direction of the catheter, but having over-all a substantially greater flow cross-section than the known lateral openings. The danger of clogging by blood is thereby reduced. However, it is also expedient for the width of the recess to increase towards the anterior edge of the catheter. By thrusting the end of the guide catheter in to different depths, therefore, the cross section through which blood can flow from the aorta into the coronary artery may be varied.

Another refinement of the invention consists in that the catheter, in manner known per se, is made of a more yielding material in the region of the recess than elsewhere. Through this yieldingness, in the known catheter a lateral flexibility and an improved insertion into the entrance opening of a coronary artery is to be achieved. The cross section of this known catheter does not vary. In the case of the catheter according to the invention, the recess permits a reduction of the cross section of the catheter, so that, according to the shape, width and length of the recess, the catheter may take on a more or less constricted or tapered shape, additionally facilitating introduction into the opening of the coronary artery. Thus the invention not only ensures blood supply and prevents the loss of contrast medium, but also facilitates insertion into the entrance opening of the coronary artery.

DETAILED DESCRIPTION OF THE INVENTION

Figure 3:
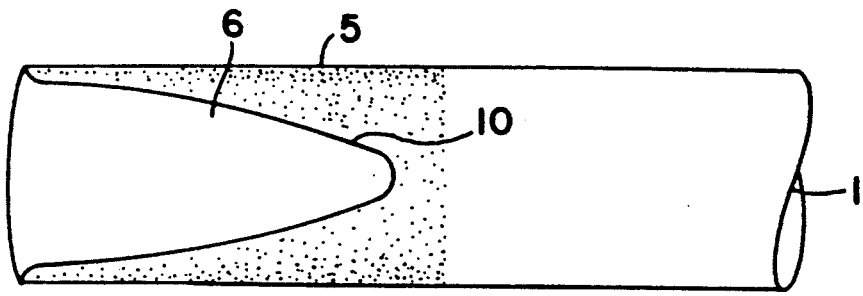

The invention will be further illustrated with reference to the drawing.

Figure 4:
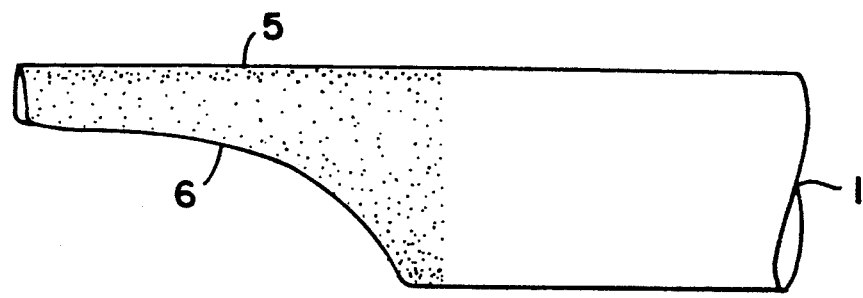
Figure 5:
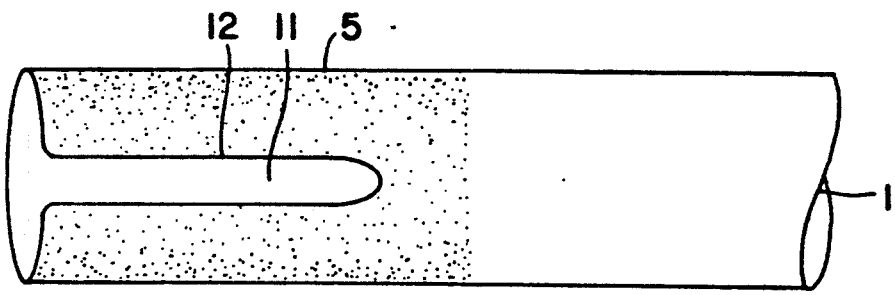
Figure 6:
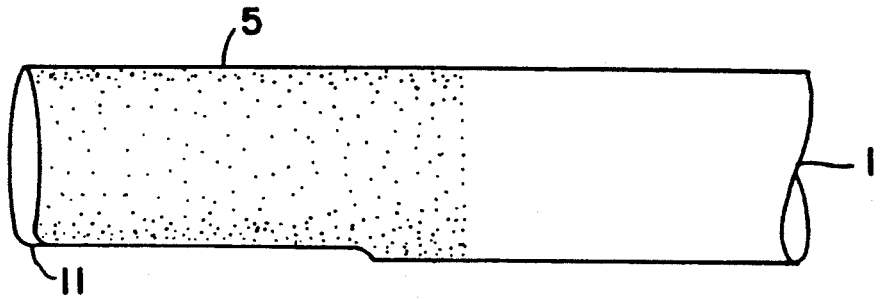

FIG. 1 shows an embodiment of a guide catheter according to the invention, by way of example, to a small scale, FIG. 2 shows the end of the guide catheter of FIG. 1, enlarged, in the region of an aorta and coronary artery, FIG. 3 shows the exterior end of the catheter of FIG. 1, much enlarged, towards a recess according to the invention, FIG. 4 is a side view of FIG. 3, FIG. 5 shows a modification in the representation of FIG. 3, and FIG. 6 is a side view of FIG. 5.

FIG. 1 shows a guide catheter 1 provided at its posterior end with a connection 2 and curved in its anterior region firstly in a large arc 3 in one direction and secondly in a smaller arc 4 in a different direction.

FIG. 2 in particular shows that the extreme end 5 exhibits a recess 6 formed by cutting it off obliquely.

The guide catheter 1 is located in an aorta 7, its exterior end 5 protruding partly into an entrance opening 8 of a coronary artery 9. In this position, the recess 6 has a large access cross-section from the aorta 7, so that blood can flow into the interior of the tubular guide catheter and on into the entrance opening 8 and the coronary artery 9. In this position as shown, a guide wire as well as a balloon catheter may already be introduced.

If contrast medium is to be injected, the end 5 of the guide catheter 1 can be inserted by suitable manipulation to the left in the drawing and hence into the entrance opening 8 of the coronary artery 9 so that the recess 6 lies entirely within the region of the entrance opening 8. This advancement takes place only briefly during the injection of contrast medium. Then the end 5 is immediately drawn back into the position shown in FIG. 2, so that blood can again flow in and through, and the blood supply of the coronary artery is restored.

FIG. 3 shows the outer tip 5 of the guide catheter 1 in the region of the recess 6, the direction of the view being at said recess 6. FIG. 4 is a side view of FIG. 3. It will be seen that the wall of the tip 5 is not cut away straight, but in the form of an S-curve, so that in the top view of FIG. 3 the edge 10 of the recess 6 forms approximately a bell-shaped curve. The tip 5 is of a more yielding material than the rest of the guide catheter 1. This yielding material is indicated by stippling.

FIGS. 5 and 6 correspond substantially to FIGS. 3 and 4. Like parts are marked with like reference numerals. The difference is that a recess 10 has substantially parallel edges 12, forming a straight slit open towards the anterior edge of the end 5.

The conformation of the tip of the guide catheter according to the invention avoids a completely tight closure of the guide catheter at the entrance of the coronary artery. Should a tight closure nevertheless occur, this will be duly indicated by a pressure drop on the manometer. By retracting the catheter, the flow can be instantly restored without losing the placement of the guide catheter.

The danger of clotting is less with the catheter according to the invention than for the known catheter with holes, since the guide catheter has only this one opening, which is flushed as usual. Besides, no contrast medium will be lost into the aorta, since the opening area can be reduced by displacement, unlike lateral holes, which are not adjustable. A safe operation with reduced danger of ischemia and optimization of visualization of the coronary arteries by means of contrast medium are assured.

I claim:

1. An intracorporeal guide catheter comprising an elongated flexible tubular member having proximal and distal ends and a wall which defines a single concentric lumen extending the entire wall of said tubular member and open longitudinally axially at each end thereof, said wall having at the distal end of the catheter a lateral portion removed therefrom to thereby provide a gap in said wall extending proximally from the tip of said distal end, with the width of the gap being uniform for its entire length.

2. An intracorporeal guide catheter comprising an elongated flexible tubular member having proximal and distal ends and a wall which defines a single concentric lumen extending the entire length of said tubular member and open longitudinally axially at each end thereof, said wall having at the distal end of the catheter a lateral portion removed therefrom to thereby provide a gap in said wall extending proximally from the tip of said distal end, wherein the width of the gap bilaterally diminishes symmetrically and non-uniformly along its length in a bell-shaped pattern.

3. An intracorporeal guide catheter adapted to guide a dilatation balloon catheter into a coronary artery of a heart comprising an elongated flexible tubular member having proximal and distal ends and a wall which defines a single concentric lumen extending the entire length of said tubular member and open longitudinally axially at each end thereof, said wall having at the distal end of the catheter a lateral portion removed therefrom to thereby provide a gap in said wall extending proximally from the tip of said distal end, with said gap being dimensioned and configured to allow blood flow through the gap from outside of said wall and into said lumen with the distal end of said catheter being located in said coronary artery.

* * * * *